(12) United States Patent
Mager et al.

(10) Patent No.: US 10,920,312 B2
(45) Date of Patent: Feb. 16, 2021

(54) ELECTROCHEMICAL CELL WITH INCREASED CURRENT DENSITY

(71) Applicant: Roche Sequencing Solutions, Inc., Pleasanton, CA (US)

(72) Inventors: Morgan Mager, Sunnyvale, CA (US); John Foster, Mountain View, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

(21) Appl. No.: 14/841,120

(22) Filed: Aug. 31, 2015

(65) Prior Publication Data

US 2017/0058397 A1 Mar. 2, 2017

(51) Int. Cl.
*C23C 14/35* (2006.01)
*C12Q 1/6874* (2018.01)
*C23C 14/06* (2006.01)
*C23C 14/34* (2006.01)
*G01N 33/487* (2006.01)

(52) U.S. Cl.
CPC ............ *C23C 14/35* (2013.01); *C12Q 1/6874* (2013.01); *C23C 14/0641* (2013.01); *C23C 14/3414* (2013.01); *G01N 33/48721* (2013.01)

(58) Field of Classification Search
CPC ............ H01M 2/14; H01M 2/26; H01M 4/00; H01M 2004/021; H01M 6/06; G01N 27/403; G01N 27/3275; G01N 27/40; G01N 27/327; G01N 27/44791; G01N 33/48721; G01N 33/48728; G01N 27/3278; C23C 14/35; C23C 14/0641; C23C 14/3414; C12Q 1/6874
See application file for complete search history.

(56) References Cited

U.S. PATENT DOCUMENTS

| | | | | |
|---|---|---|---|---|
| 2009/0032401 | A1* | 2/2009 | Ronaghi | B01L 3/502761 204/549 |
| 2014/0034497 | A1* | 2/2014 | Davis | G01N 27/44791 204/451 |
| 2015/0137275 | A1* | 5/2015 | Musa | G01N 27/30 257/414 |

FOREIGN PATENT DOCUMENTS

WO 2015061510 A1 4/2015

OTHER PUBLICATIONS

International Search report and written opinion dated Dec. 7, 2016 received in corresponding PCT application No. PCT/EP2016/070195 filed on Aug. 26, 2016, pp. 1-10.

* cited by examiner

*Primary Examiner* — Bethany L Martin
(74) *Attorney, Agent, or Firm* — Roche Sequencing Solutions, Inc.

(57) ABSTRACT

A nanopore cell is disclosed. The nanopore cell includes an electrolyte well having a bottom base, a surrounding sidewall, and a hydrophobic surface above the surrounding sidewall. The nanopore cell further includes a first layer of electrode material disposed on the bottom base of the electrolyte well. The nanopore cell further includes a second layer of electrode material disposed on the surrounding sidewall of the electrolyte well and electrically connected to the first layer of electrode material. The first layer of electrode material and the second layer of electrode material are configured to jointly provide capacitive coupling when an electrolyte is placed in the electrolyte well.

6 Claims, 18 Drawing Sheets

ELECTROCHEMICAL CELL WITH INCREASED CURRENT DENSITY

BACKGROUND OF THE INVENTION

Advances in micro-miniaturization within the semiconductor industry in recent years have enabled biotechnologists to begin packing traditionally bulky sensing tools into smaller and smaller form factors, onto so-called biochips. It would be desirable to develop techniques for biochips that make them more robust, efficient, and cost-effective.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions across the nanopore can be observed. The size of the current is sensitive to the pore size.

A nanopore based sequencing chip may be used for DNA sequencing. A nanopore based sequencing chip incorporates a large number of sensor cells configured as an array. For example, an array of one million cells may include 1000 rows by 1000 columns of cells.

Figure 1:
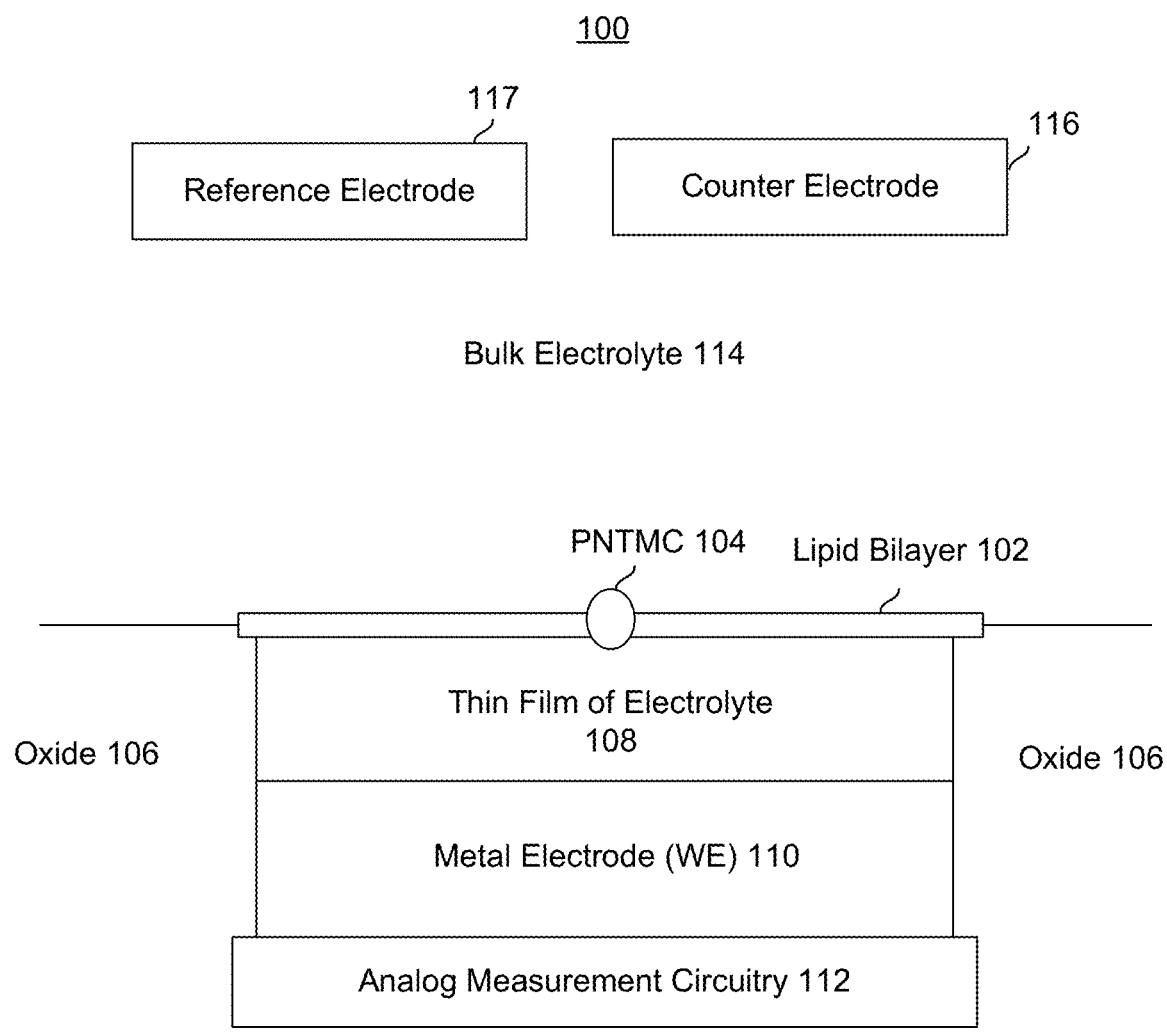
FIG. 1 illustrates an embodiment of a cell 100 in a nanopore based sequencing chip.

FIG. 1 illustrates an embodiment of a cell 100 in a nanopore based sequencing chip. A membrane 102 is formed over the surface of the cell. In some embodiments, membrane 102 is a lipid bilayer. The bulk electrolyte 114 containing protein nanopore transmembrane molecular complexes (PNTMC) and the analyte of interest is placed directly onto the surface of the cell. A single PNTMC 104 is inserted into membrane 102 by electroporation. The individual membranes in the array are neither chemically nor electrically connected to each other. Thus, each cell in the array is an independent sequencing machine, producing data unique to the single polymer molecule associated with the PNTMC. PNTMC 104 operates on the analytes and modulates the ionic current through the otherwise impermeable bilayer.

With continued reference to FIG. 1, analog measurement circuitry 112 is connected to an electrode 110 covered by a thin film of electrolyte 108. The thin film of electrolyte 108 is isolated from the bulk electrolyte 114 by the ion-impermeable membrane 102. PNTMC 104 crosses membrane 102 and provides the only path for ionic current to flow from the bulk liquid to working electrode 110. The cell also includes a counter electrode (CE) 116. The cell also includes a reference electrode 117, which acts as an electrochemical potential sensor.

Figure 2:
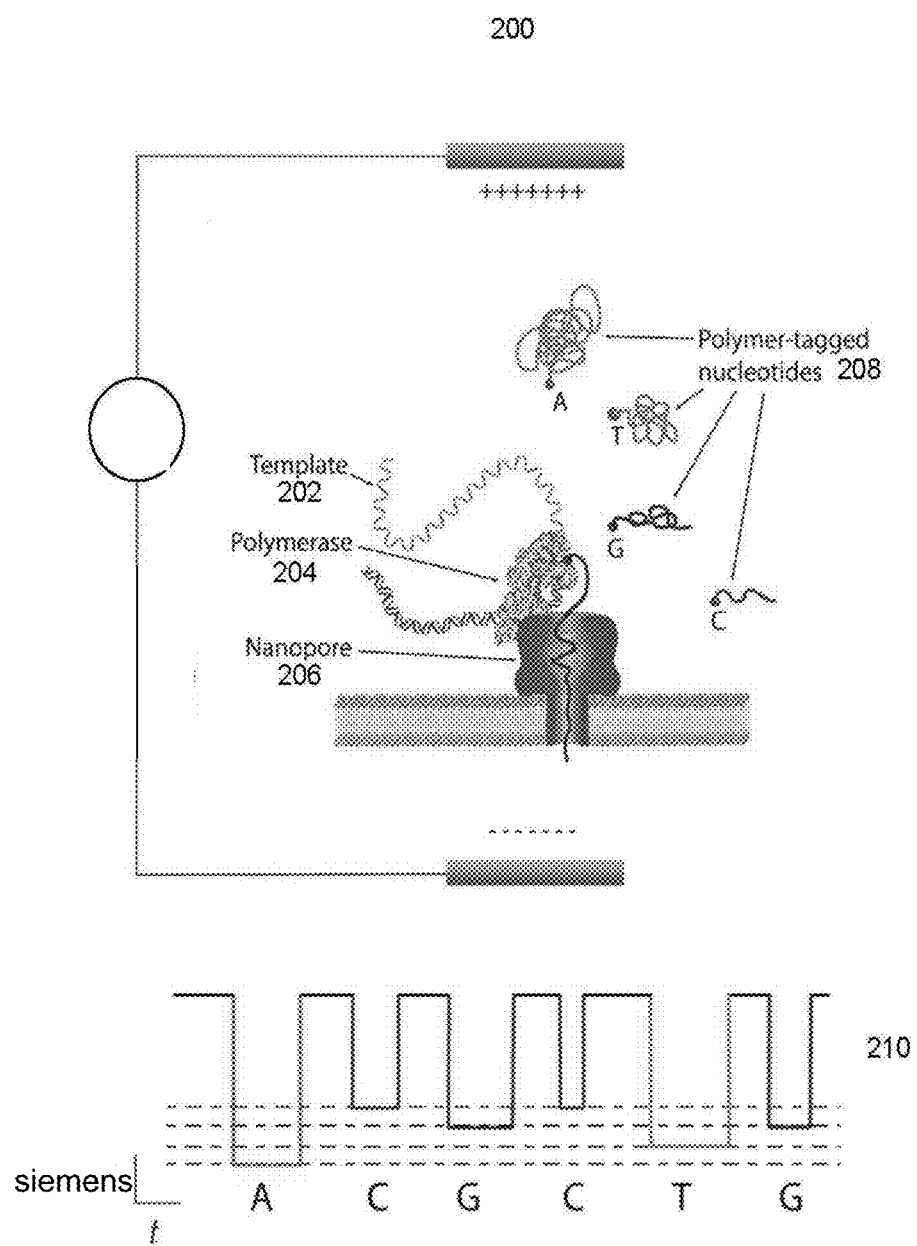
FIG. 2 illustrates an embodiment of a cell 200 performing nucleotide sequencing with the Nano-SBS technique.

In some embodiments, a nanopore array enables parallel sequencing using the single molecule nanopore-based sequencing by synthesis (Nano-SBS) technique. FIG. 2 illustrates an embodiment of a cell 200 performing nucleotide sequencing with the Nano-SBS technique. In the Nano-SBS technique, a template 202 to be sequenced and a primer are introduced to cell 200. To this template-primer complex, four differently tagged nucleotides 208 are added to the bulk aqueous phase. As the correctly tagged nucleotide is complexed with the polymerase 204, the tail of the tag is positioned in the barrel of nanopore 206. The tag held in the barrel of nanopore 206 generates a unique ionic blockade signal 210, thereby electronically identifying the added base due to the tags' distinct chemical structures.

Figure 3:
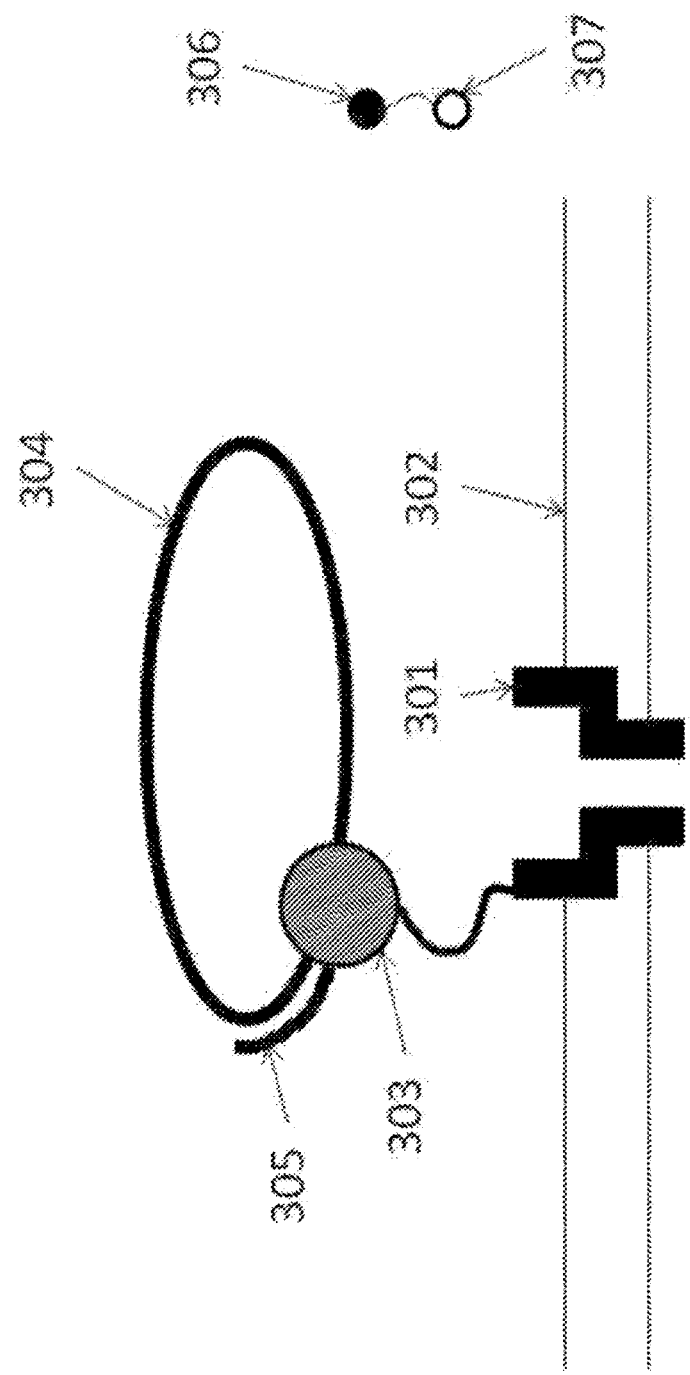
FIG. 3 illustrates an embodiment of a cell about to perform nucleotide sequencing with pre-loaded tags.

FIG. 3 illustrates an embodiment of a cell about to perform nucleotide sequencing with pre-loaded tags. A nanopore 301 is formed in a membrane 302. An enzyme 303 (e.g., a polymerase, such as a DNA polymerase) is associated with the nanopore. In some cases, polymerase 303 is covalently attached to nanopore 301. Polymerase 303 is associated with a nucleic acid molecule 304 to be sequenced. In some embodiments, the nucleic acid molecule 304 is circular. In some cases, nucleic acid molecule 304 is linear. In some embodiments, a nucleic acid primer 305 is hybridized to a portion of nucleic acid molecule 304. Polymerase 303 catalyzes the incorporation of nucleotides 306 onto primer 305 using single stranded nucleic acid molecule 304 as a template. Nucleotides 306 comprise tag species ("tags") 307.

Figure 4:
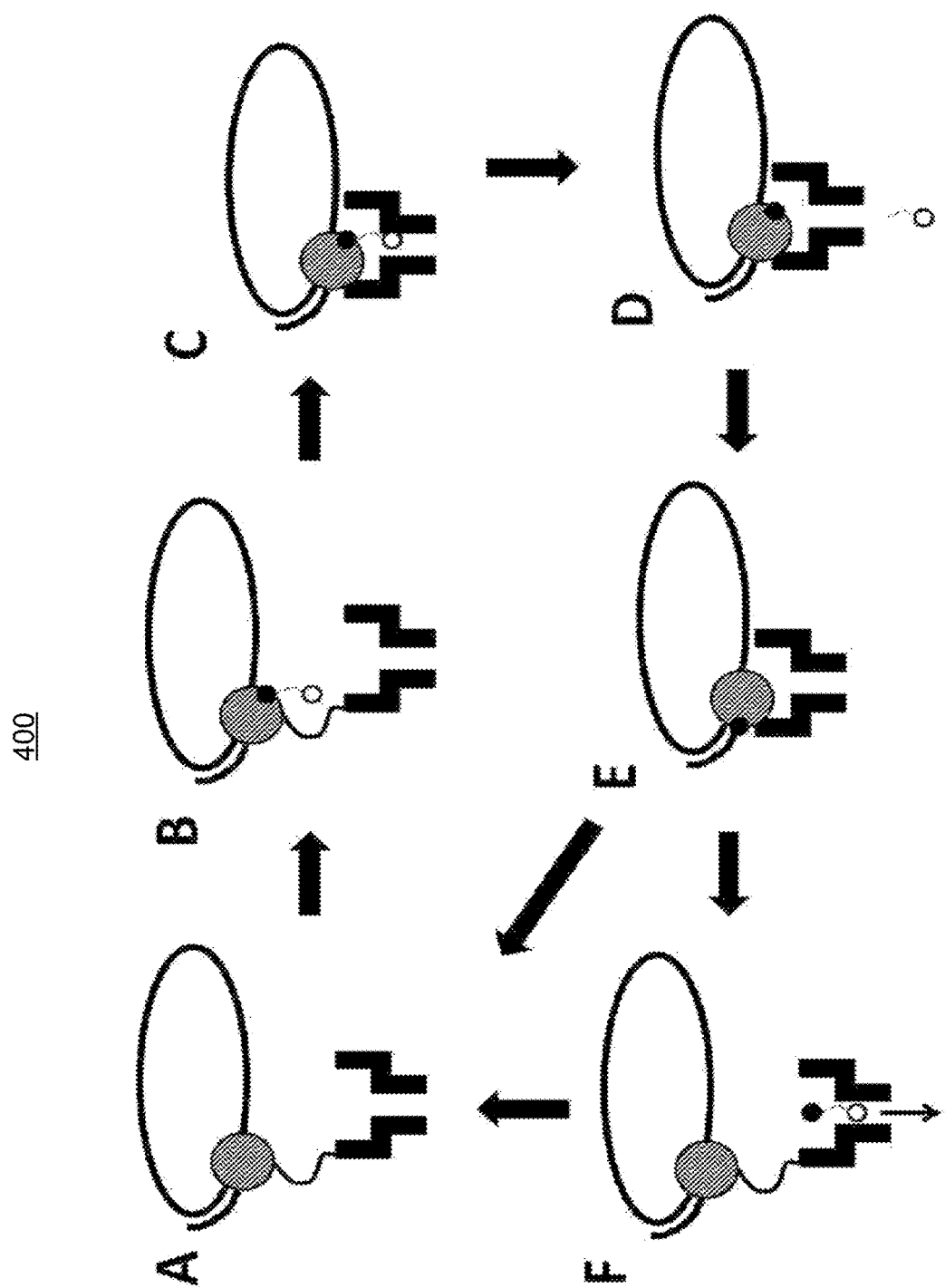
FIG. 4 illustrates an embodiment of a process 400 for nucleic acid sequencing with pre-loaded tags.

FIG. 4 illustrates an embodiment of a process 400 for nucleic acid sequencing with pre-loaded tags. At stage A, a tagged nucleotide (one of four different types: A, T, G, or C) is not associated with the polymerase. At stage B, a tagged nucleotide is associated with the polymerase. At stage C, the polymerase is in close proximity to the nanopore. The tag is pulled into the nanopore by an electrical field generated by a voltage applied across the membrane and/or the nanopore.

Some of the associated tagged nucleotides are not base paired with the nucleic acid molecule. These non-paired nucleotides typically are rejected by the polymerase within a time scale that is shorter than the time scale for which correctly paired nucleotides remain associated with the polymerase. Since the non-paired nucleotides are only transiently associated with the polymerase, process 400 as shown in FIG. 4 typically does not proceed beyond stage B.

Before the polymerase is docked to the nanopore, the conductance of the nanopore is ~300 pico Siemens (300 pS). At stage C, the conductance of the nanopore is about 60 pS, 80 pS, 100 pS, or 120 pS corresponding to one of the four types of tagged nucleotides. The polymerase undergoes an isomerization and a transphosphorylation reaction to incorporate the nucleotide into the growing nucleic acid molecule and release the tag molecule. In particular, as the tag is held in the nanopore, a unique conductance signal (e.g., see signal 210 in FIG. 2) is generated due to the tag's distinct chemical structures, thereby identifying the added base electronically. Repeating the cycle (i.e., stage A through E or stage A through F) allows for the sequencing of the nucleic acid molecule. At stage D, the released tag passes through the nanopore.

In some cases, tagged nucleotides that are not incorporated into the growing nucleic acid molecule will also pass through the nanopore, as seen in stage F of FIG. 4. The unincorporated nucleotide can be detected by the nanopore in some instances, but the method provides a means for distinguishing between an incorporated nucleotide and an unincorporated nucleotide based at least in part on the time for which the nucleotide is detected in the nanopore. Tags bound to unincorporated nucleotides pass through the nanopore quickly and are detected for a short period of time (e.g., less than 10 ms), while tags bound to incorporated nucleotides are loaded into the nanopore and detected for a long period of time (e.g., at least 10 ms).

Figure 5:
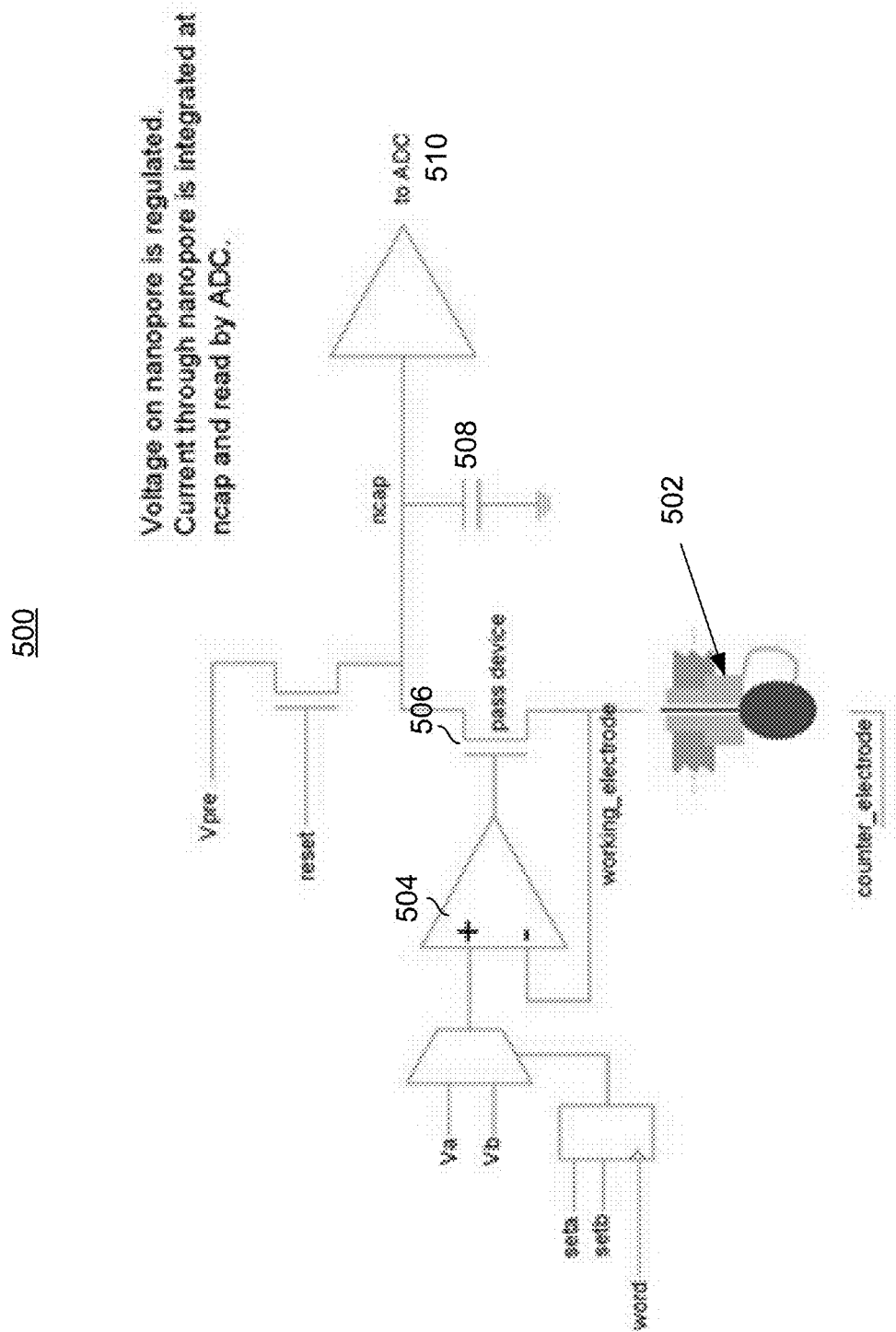
FIG. 5 illustrates an embodiment of a circuitry 500 in a cell of a nanopore based sequencing chip.

FIG. 5 illustrates an embodiment of a circuitry 500 in a cell of a nanopore based sequencing chip. As mentioned above, when the tag is held in nanopore 502, a unique conductance signal (e.g., see signal 210 in FIG. 2) is generated due to the tag's distinct chemical structures, thereby identifying the added base electronically. The circuitry in FIG. 5 maintains a constant voltage across nanopore 502 when the current flow is measured. In particular, the circuitry includes an operational amplifier 504 and a pass device 506 that maintain a constant voltage equal to $V_a$ or $V_b$ across nanopore 502. The current flowing through nanopore 502 is integrated at a capacitor $n_{cap}$ 508 and measured by an Analog-to-Digital (ADC) converter 510.

However, circuitry 500 has a number of drawbacks. One of the drawbacks is that circuitry 500 only measures unidirectional current flow. Another drawback is that operational amplifier 504 in circuitry 500 may introduce a number of performance issues. For example, the offset voltage and the temperature drift of operational amplifier 504 may cause the actual voltage applied across nanopore 502 to vary across different cells. The actual voltage applied across nanopore 502 may drift by tens of millivolts above or below the desired value, thereby causing significant measurement inaccuracies. In addition, the operational amplifier noise may cause additional detection errors. Another drawback is that the portions of the circuitry for maintaining a constant voltage across the nanopore while current flow measurements are made are area-intensive. For example, operational amplifier 504 occupies significantly more space in a cell than other components. As the nanopore based sequencing chip is scaled to include more and more cells, the area occupied by the operational amplifiers may increase to an unattainable size. Unfortunately, shrinking the operational amplifier's size in a nanopore based sequencing chip with a large-sized array may raise other performance issues. For example, it may exacerbate the offset and noise problems in the cells even further.

Figure 6:
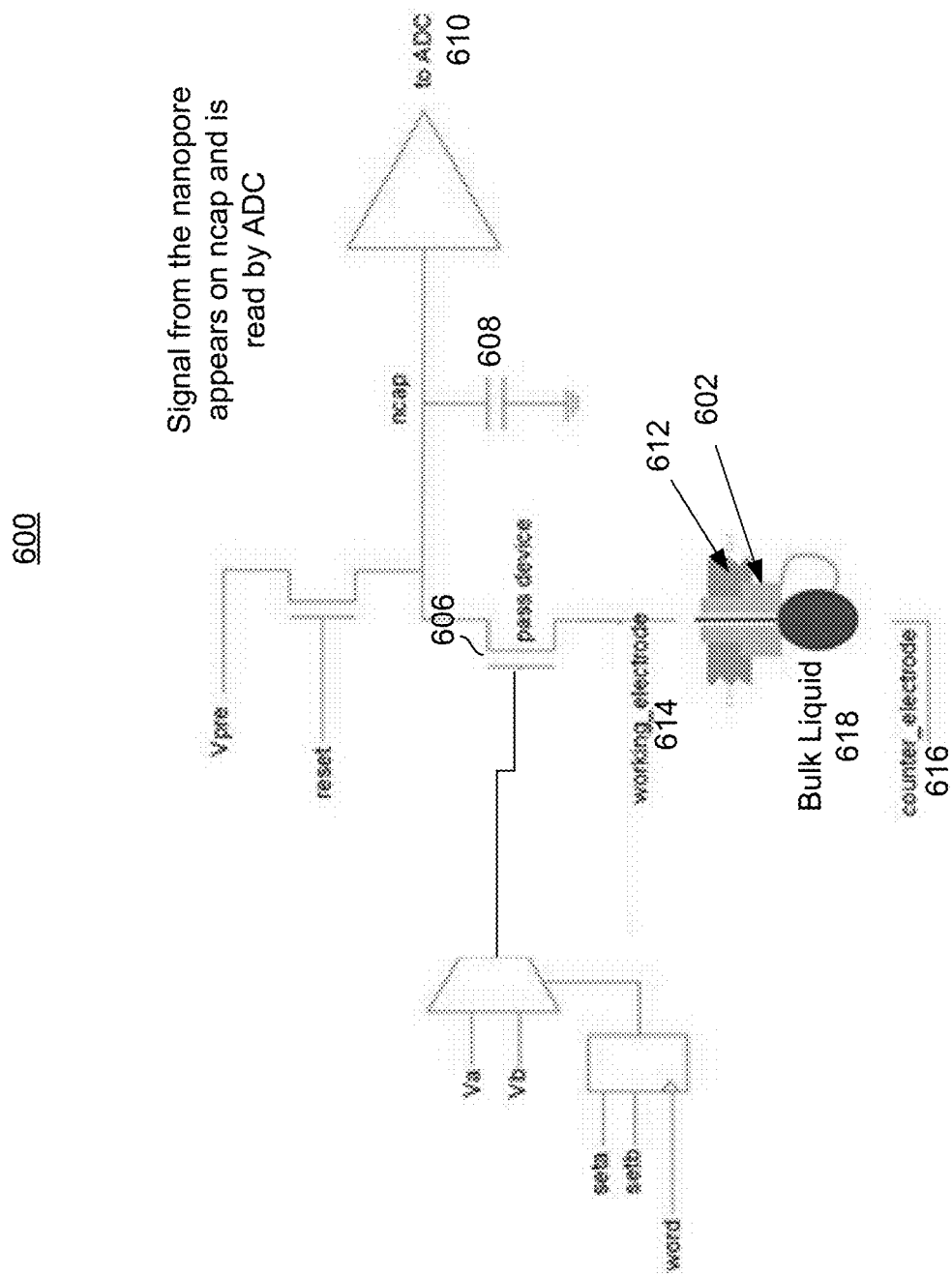
FIG. 6 illustrates an embodiment of a circuitry 600 in a cell of a nanopore based sequencing chip, wherein the voltage applied across the nanopore can be configured to vary over a time period during which the nanopore is in a particular detectable state.
Figure 7A:
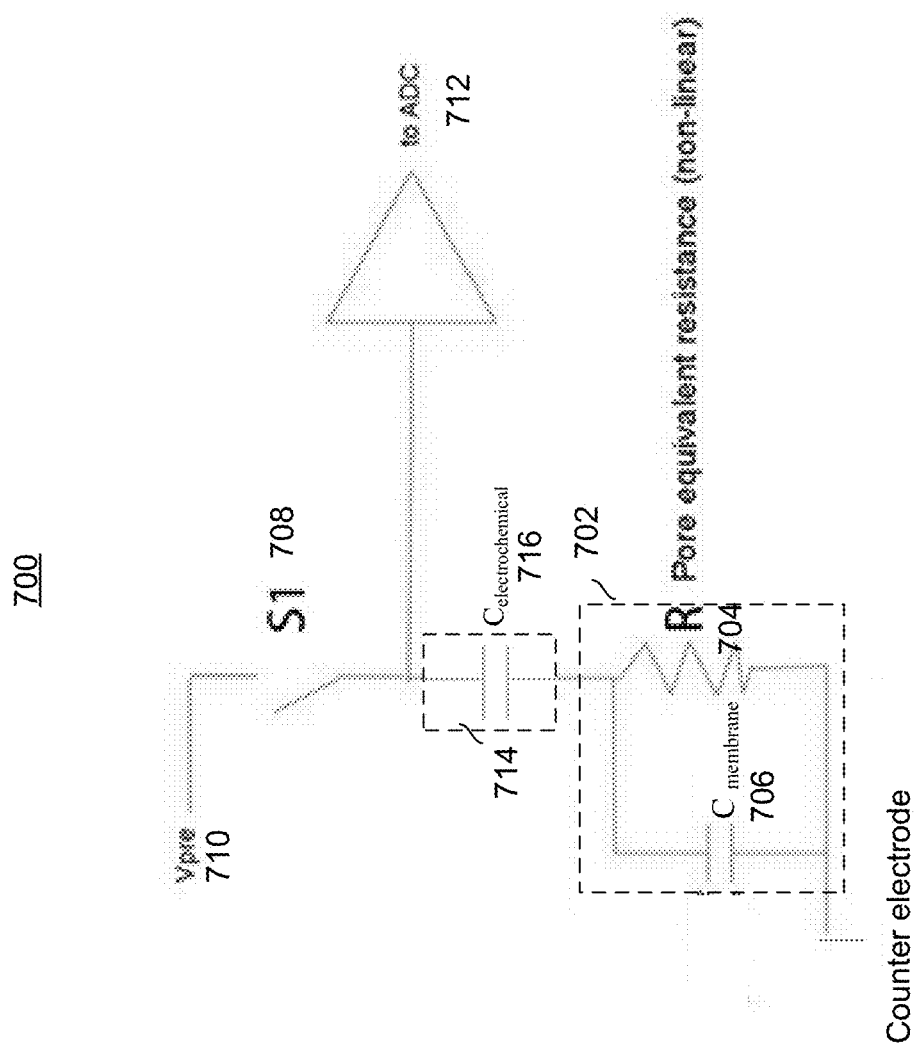
FIG. 7A illustrates an additional embodiment of a circuitry 700 in a cell of a nanopore based sequencing chip, wherein the voltage applied across the nanopore can be configured to vary over a time period during which the nanopore is in a particular detectable state.
Figure 7B:
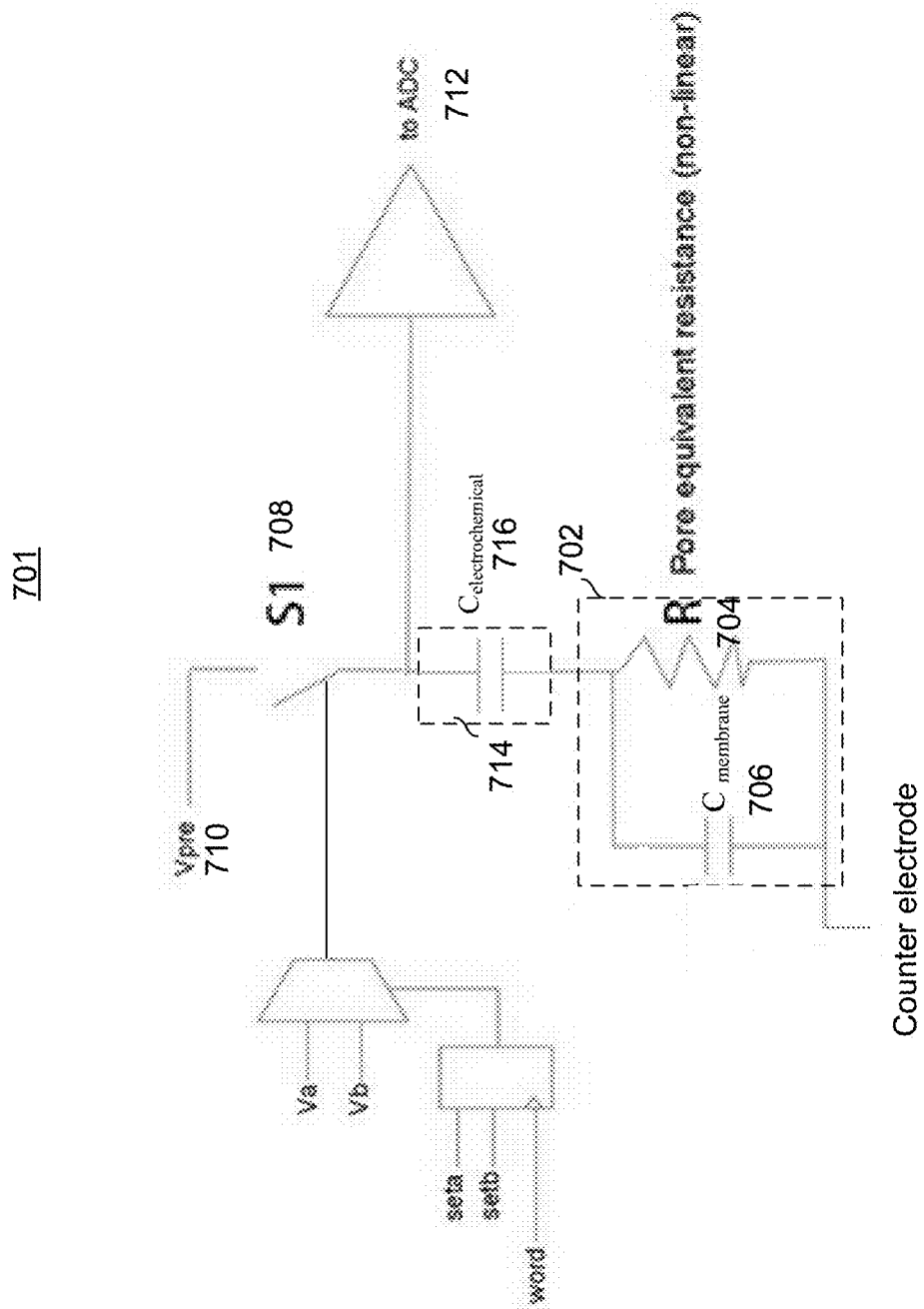
FIG. 7B illustrates an additional embodiment of a circuitry 701 in a cell of a nanopore based sequencing chip, wherein the voltage applied across the nanopore can be configured to vary over a time period during which the nanopore is in a particular detectable state.

FIG. 6 illustrates an embodiment of a circuitry 600 in a cell of a nanopore based sequencing chip, wherein the voltage applied across the nanopore can be configured to vary over a time period during which the nanopore is in a particular detectable state. One of the possible states of the nanopore is an open-channel state when a tag-attached polyphosphate is absent from the barrel of the nanopore. Another four possible states of the nanopore correspond to the states when the four different types of tag-attached polyphosphate (A, T, G, or C) are held in the barrel of the nanopore. Yet another possible state of the nanopore is when the membrane is ruptured. FIGS. 7A and 7B illustrate additional embodiments of a circuitry (700 and 701) in a cell of a nanopore based sequencing chip, wherein the voltage applied across the nanopore can be configured to vary over a time period during which the nanopore is in a particular detectable state. In the above circuits, the operational amplifier is no longer required.

FIG. 6 shows a nanopore 602 that is inserted into a membrane 612, and nanopore 602 and membrane 612 are situated between a cell working electrode 614 and a counter electrode 616, such that a voltage is applied across nanopore 602. Nanopore 602 is also in contact with a bulk liquid/electrolyte 618. Note that nanopore 602 and membrane 612 are drawn upside down as compared to the nanopore and membrane in FIG. 1. Hereinafter, a cell is meant to include at least a membrane, a nanopore, a working cell electrode, and the associated circuitry. In some embodiments, the counter electrode is shared between a plurality of cells, and is therefore also referred to as a common electrode. The common electrode can be configured to apply a common potential to the bulk liquid in contact with the nanopores in the measurements cells. The common potential and the common electrode are common to all of the measurement cells. There is a working cell electrode within each measurement cell; in contrast to the common electrode, working cell electrode 614 is configurable to apply a distinct potential that is independent from the working cell electrodes in other measurement cells.

In FIGS. 7A and 7B, instead of showing a nanopore inserted in a membrane and the liquid surrounding the nanopore, an electrical model 702 representing the electrical properties of the nanopore and the membrane and an electrical model 714 representing the electrical properties of the working electrode are shown. Note in FIGS. 7A and 7B that the respective circuitry does not require an extra capacitor (e.g., $n_{cap}$ 508 in FIG. 5) to be fabricated on-chip, thereby facilitating the reduction in size of the nanopore based sequencing chip.

Electrical model 702 includes a capacitor 706 that models a capacitance associated with the membrane ($C_{membrane}$) and a resistor 704 that models a resistance associated with the nanopore in different states (e.g., the open-channel state or the states corresponding to having different types of tags or molecules inside the nanopore). Electrical model 714 includes a capacitor 716 that models a capacitance associated with the working electrode. The capacitance associated with the working electrode is also referred to as an electrochemical capacitance ($C_{electrochemical}$). The electrochemical capacitance $C_{electrochemical}$ associated with the working electrode includes a double-layer capacitance and may further include a pseudocapacitance.

Figure 7C:
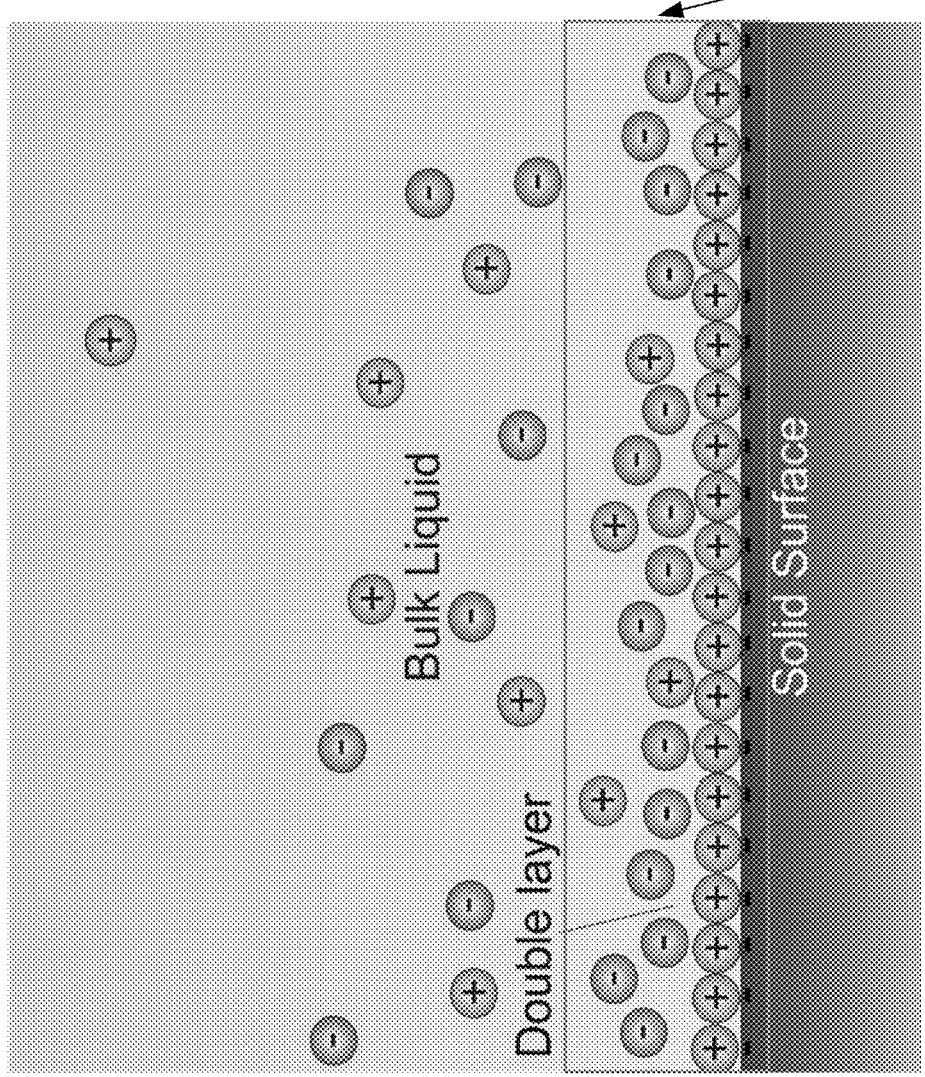
FIG. 7C illustrates a double layer that is formed at any interface between a conductive electrode and an adjacent liquid electrolyte. In the example shown, the electrode surface is negatively charged, resulting in the accumulation of positively charged species in the electrolyte. In another example, the polarity of all charges shown may be opposite to the example shown.
Figure 7D:
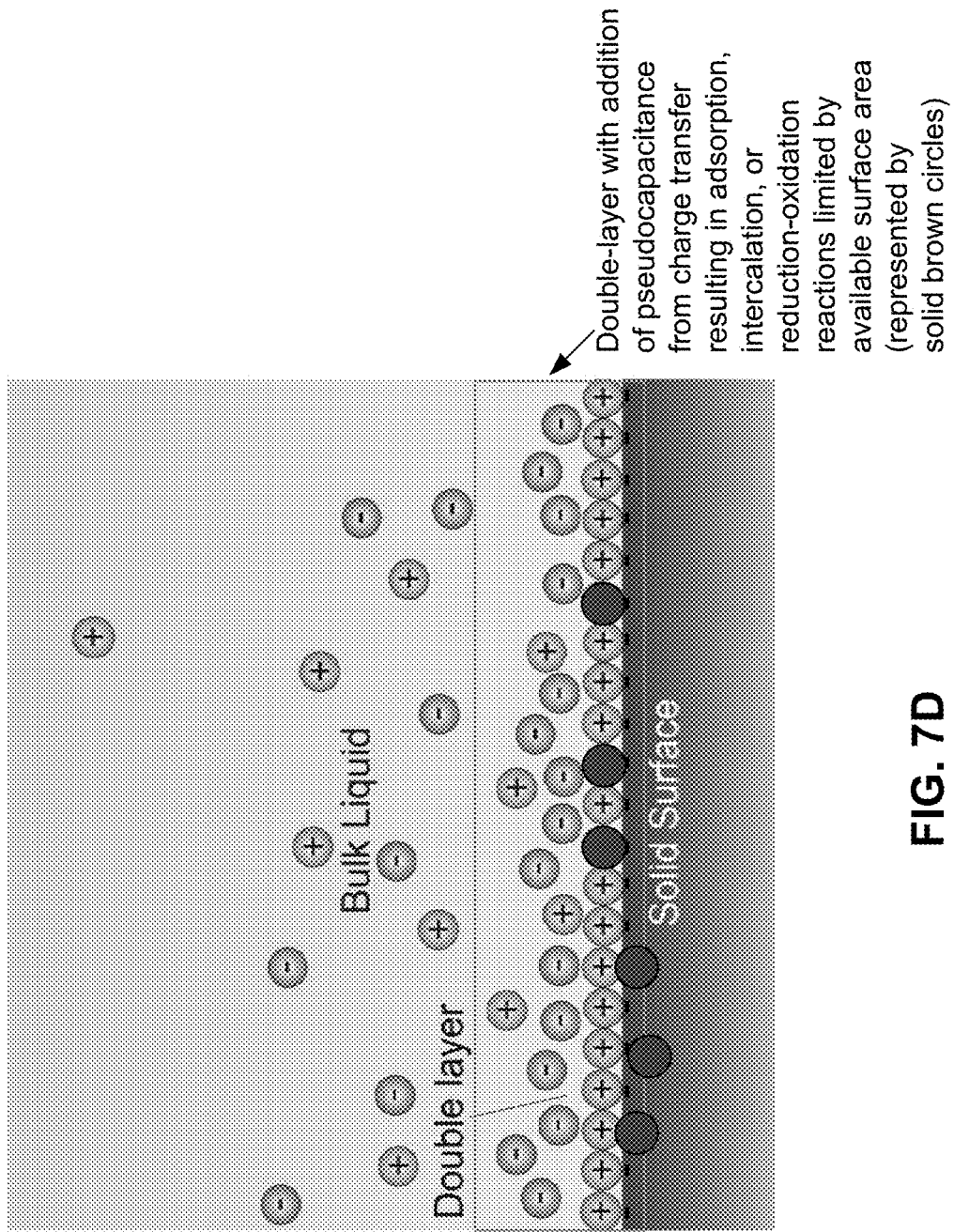
FIG. 7D illustrates a pseudocapacitance effect that can be formed, simultaneously with the formation of a double-layer as in FIG. 7C, at an interface between a conductive electrode and an adjacent liquid electrolyte.

FIG. 7C illustrates a double layer that is formed at any interface between a conductive electrode and an adjacent liquid electrolyte. If a voltage is applied, electronic charges (positive or negative) accumulate in the electrode at the interface between the conductive electrode and adjacent liquid electrolyte. The charge in the electrode is balanced by reorientation of dipoles and accumulation of ions of opposite charge in the electrolyte near the interface. The accumulation of charges on either side of the interface between electrode and electrolyte, separated by a small distance due to the finite size of charged species and solvent molecules in the electrolyte, acts like a dielectric in a conventional capacitor. The term "double layer" refers to the ensemble of electronic and ionic charge distribution in the vicinity of the interface between the electrode and electrolyte. FIG. 7D illustrates a pseudocapacitance effect that can be formed, simultaneously with the formation of a double-layer as in FIG. 7C, at an interface between a conductive electrode and an adjacent liquid electrolyte. A pseudocapacitor stores electrical energy faradaically by electron charge transfer between the electrode and the electrolyte. This is accomplished through electrosorption, reduction-oxidation reactions, or intercalation processes.

Figure 8:
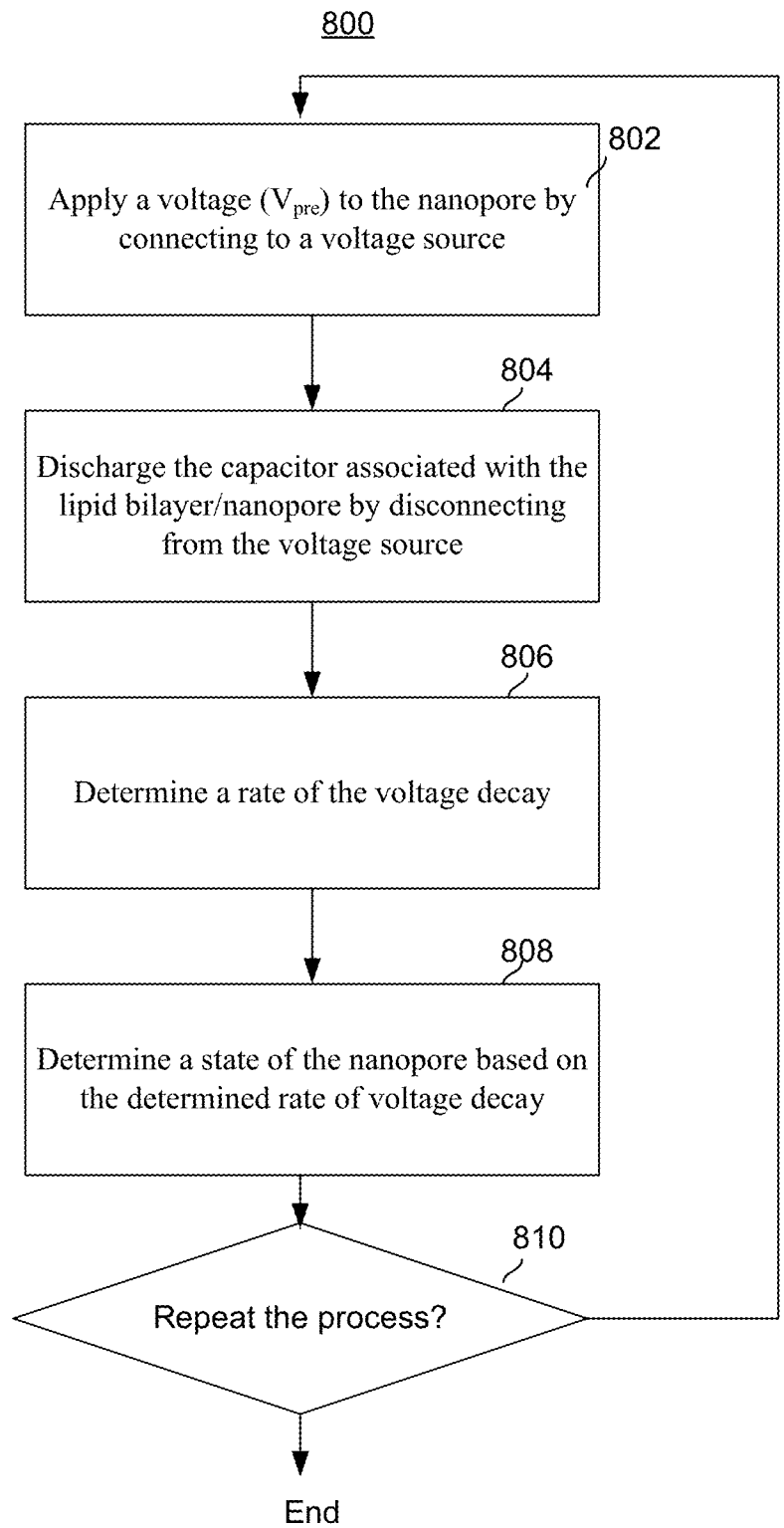
FIG. 8 illustrates an embodiment of a process 800 for analyzing a molecule inside a nanopore, wherein the nanopore is inserted in a membrane.
Figure 9:
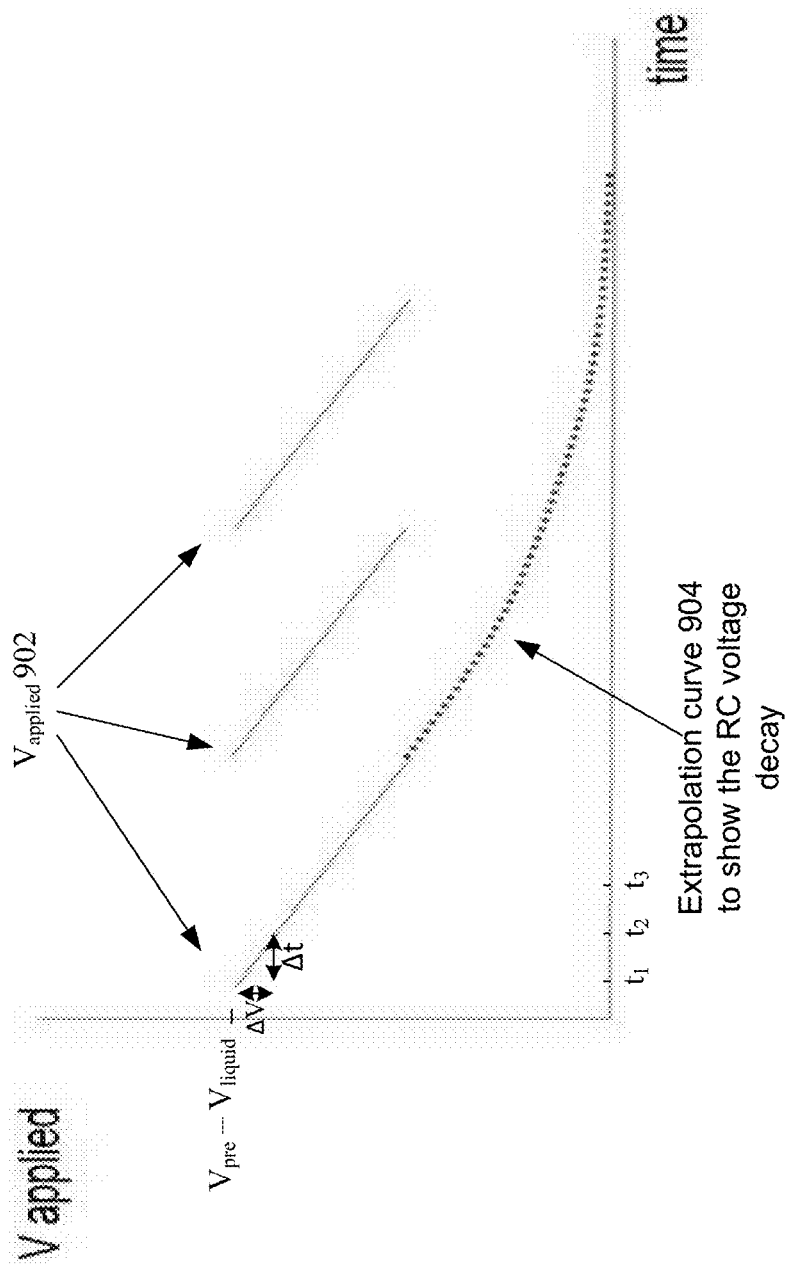
FIG. 9 illustrates an embodiment of a plot of the voltage applied across the nanopore versus time when process 800 is performed and repeated three times.

FIG. 8 illustrates an embodiment of a process 800 for analyzing a molecule inside a nanopore, wherein the nanopore is inserted in a membrane. Process 800 may be performed using the circuitries shown in FIG. 6, 7A, or 7B. FIG. 9 illustrates an embodiment of a plot of the voltage applied across the nanopore versus time when process 800 is performed and repeated three times. The voltage across the nanopore changes over time. The rate of the voltage decay (i.e., the steepness of the slope of the voltage across the nanopore versus time plot) depends on the cell resistance (e.g., the resistance of resistor 704 in FIG. 7A). More particularly, as the resistances associated with the nanopore in different states (e.g., the states corresponding to having different types of molecules inside the nanopore) are different due to the molecules' distinct chemical structure, different corresponding rates of voltage decay may be observed and thus may be used to identify the molecule in the nanopore.

Figure 10:
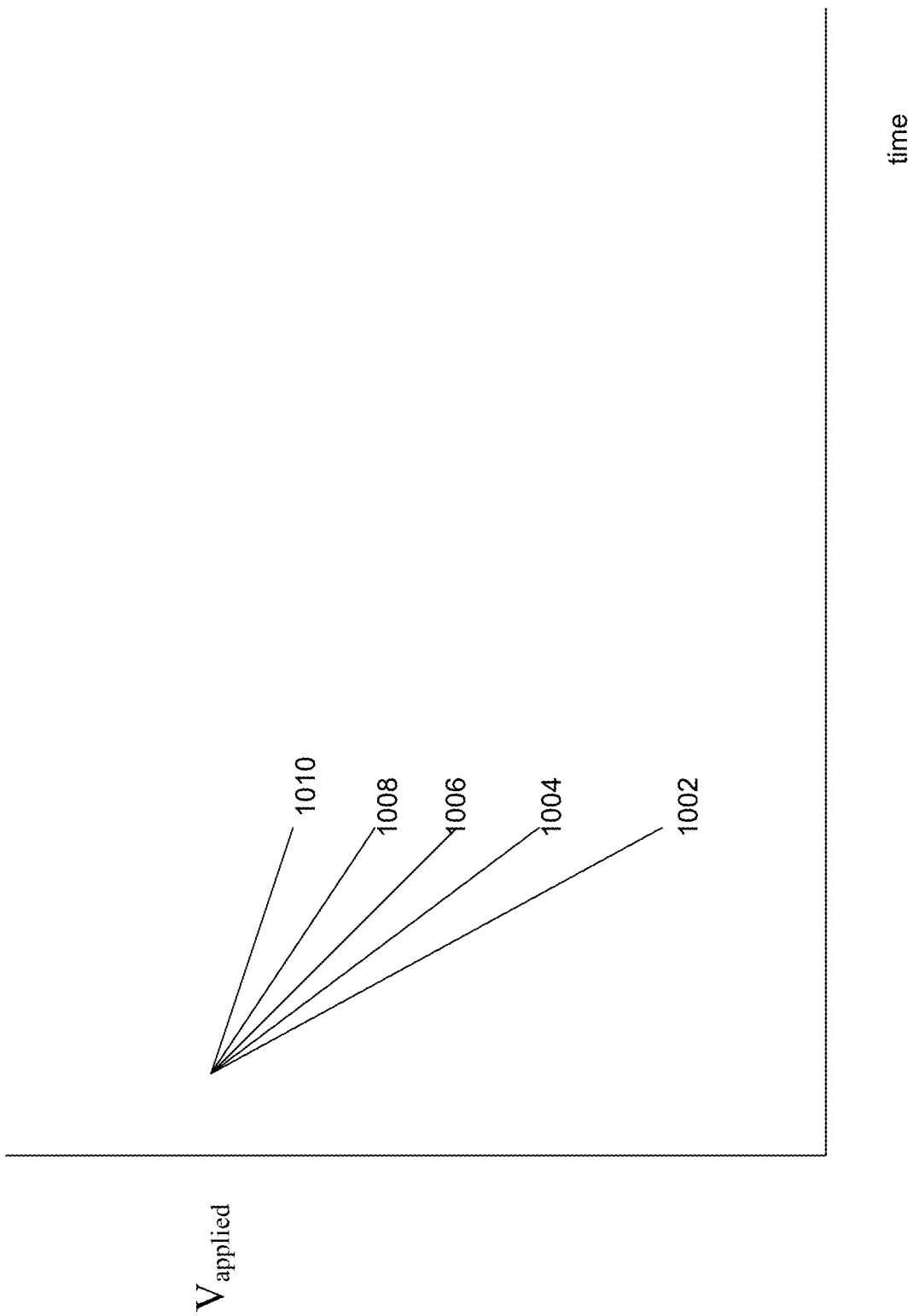
FIG. 10 illustrates an embodiment of the plots of the voltage applied across the nanopore versus time when the nanopore is in different states.

FIG. 10 illustrates the plots of the voltage applied across the nanopore versus time when the nanopore is in different states. Curve 1002 shows the rate of voltage decay during an open-channel state. In some embodiments, the resistance associated with the nanopore in an open-channel state is in the range of 100 Mohm to 20 Gohm. Curves 1004, 1006, 1008, and 1010 show the different rates of voltage decay corresponding to the four capture states when the four different types of tag-attached polyphosphate (A, T, G, or C) are held in the barrel of the nanopore. In some embodiments, the resistance associated with the nanopore in a capture state is within the range of 200 Mohm to 40 Gohm. Note that the slope of each of the plots is distinguishable from each other.

Allowing the voltage applied across the nanopore to decay over a time period during which the nanopore is in a particular detectable state has many advantages. One of the advantages is that the elimination of the operational amplifier, the pass device, and the capacitor (e.g., $n_{cap}$ 508 in FIG. 5) that are otherwise fabricated on-chip in the cell circuitry significantly reduces the footprint of a single cell in the nanopore based sequencing chip, thereby facilitating the scaling of the nanopore based sequencing chip to include more and more cells (e.g., incorporating millions of cells in a nanopore based sequencing chip). The capacitance in parallel with the nanopore includes two portions: the capacitance associated with the membrane and the capacitance associated with the integrated chip (IC). Due to the thin nature of the membrane, the capacitance associated with the membrane alone can suffice to achieve the required RC time constant without the need for additional on-chip capacitance, thereby allowing significant reduction in cell size and chip size.

Another advantage is that the circuitry of a cell does not suffer from offset inaccuracies because $V_{pre}$ is applied directly to the working electrode without any intervening circuitry. Another advantage is that since no switches are being opened or closed during the measurement intervals, the amount of charge injection is minimized.

Furthermore, the technique described above operates equally well using positive voltages or negative voltages. Bidirectional measurements have been shown to be helpful in characterizing a molecular complex. For example, they can be used to correct for baseline drift arising from AC-non-faradaic operation.

The ratio of the capacitance associated with the membrane (see $C_{membrane}$ 706 of FIGS. 7A and 7B) and the capacitance associated with the working electrode (see $C_{electrochemical}$ 716 of FIGS. 7A and 7B) may be adjusted to achieve optimal overall system performance. Increased system performance may be achieved by reducing $C_{membrane}$ while maximizing $C_{electrochemical}$. For example, $C_{membrane}$ is adjusted to achieve the required RC time constant without the need for additional on-chip capacitance, thereby allowing a significant reduction in cell size and chip size. $C_{electrochemical}$ is maximized such that the impedance associated with $C_{electrochemical}$ is close to an AC (alternating current) short circuit compared with the impedance associated with $C_{membrane}$. $C_{electrochemical}$ is also maximized such that the information signal measured by the circuitries shown in FIG. 6, 7A, or 7B becomes more stable and that the spurious signal convoluted on top of the information signal is minimized.

Figure 11:
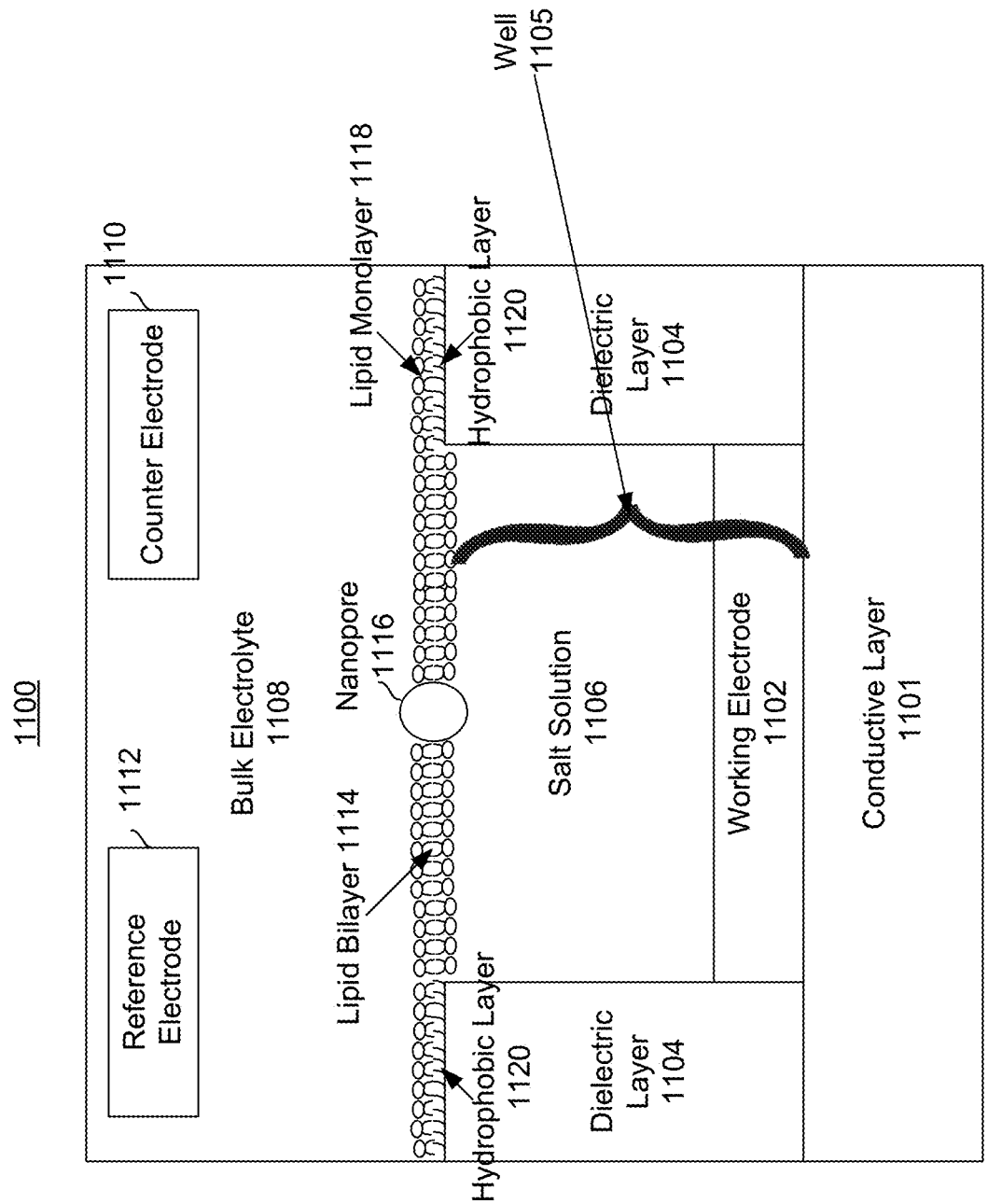
FIG. 11 illustrates an embodiment of an electrochemical cell 1100 in a nanopore based sequencing chip.

FIG. 11 illustrates an embodiment of an electrochemical cell 1100 in a nanopore based sequencing chip. In this embodiment, the ratio of the $C_{membrane}$ and $C_{electrochemical}$ may be adjusted by increasing $C_{electrochemical}$, as will be described in greater detail below.

Cell 1100 includes a conductive or metal layer 1101. Metal layer 1101 connects cell 1100 to the remaining portions of the nanopore based sequencing chip. In some embodiments, metal layer 1101 is the metal 6 layer (M6). Cell 1100 further includes a dielectric layer 1104 above conductive layer 1101. Dielectric layer 1104 forms the wall surrounding a well 1105 in which a working electrode 1102 is located at the bottom. Dielectric material used to form dielectric layer 1104 includes glass, oxide, silicon mononitride (SiN), silicon dioxide ($SiO_2$), and the like. In some embodiments, working electrode 1102 is made of materials that are resistant to corrosion and oxidation for non-faradaic conduction. In some embodiments, electrode material should be moderately hydrophilic to facilitate wetting, thereby improving electrical contact. The top surface of dielectric layer 1104 may be silanized. Silanization forms a hydrophobic layer 1120 above the top surface of dielectric layer 1104. Well 1105 formed by the dielectric layer wall 1104 further includes a film of salt solution 1106 above working electrode 1102. Salt solution 1106 may include one of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), Manganese chloride ($MnCl_2$), and magnesium chloride ($MgCl_2$).

As shown in FIG. 11, a membrane is formed on top of dielectric layer 1104 and spans across well 1105. For example, the membrane includes a lipid monolayer 1118 formed on top of hydrophobic layer 1120. As the membrane reaches the opening of well 1105, the lipid monolayer transitions to a lipid bilayer 1114 that spans across the opening of the well. A bulk electrolyte 1108 containing protein nanopore transmembrane molecular complexes (PNTMC) and the analyte of interest is placed directly above the well. Bulk electrolyte 1108 may further include one of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), manganese chloride ($MnCl_2$), and magnesium chloride ($MgCl_2$). A single PNTMC/nanopore 1116 is inserted into lipid bilayer 1114 by electroporation. Nanopore 1116 crosses lipid bilayer 1114 and provides the only path for ionic flow from bulk electrolyte 1108 to working electrode 1102.

Cell 1100 includes a counter electrode (CE) 1110. Cell 1100 also includes a reference electrode 1112, which acts as an electrochemical potential sensor. In some embodiments, counter electrode 1110 is shared between a plurality of cells, and is therefore also referred to as a common electrode. The common electrode can be configured to apply a common potential to the bulk liquid in contact with the nanopores in the measurements cells. The common potential and the common electrode are common to all of the measurement cells.

As discussed above, the ratio of $C_{membrane}$ and $C_{electrochemical}$ in cell 1100 may be adjusted by increasing $C_{electrochemical}$. The electrochemical capacitance ($C_{electrochemical}$) associated with working electrode 1102 may be increased by increasing the thickness of working electrode 1102. In some embodiments, the thickness of working electrode 1102 ranges from 10 nanometers to 1 micron.

$C_{electrochemical}$ may also be increased by maximizing the specific surface area of the electrode. The specific surface area of working electrode 1102 is the total surface area of the electrode per unit of mass (e.g., $m^2/kg$), per unit of volume (e.g., $m^2/m^3$ or $m^{-1}$), or per unit of base area (e.g., $m^2/m^2$). As the specific surface area increases, the electrochemical capacitance ($C_{electrochemical}$) increases, and a greater amount of ions can be displaced with the same applied potential before the capacitor becomes charged. For example, the specific surface area of the working electrode may be increased by making the electrode "spongy."

Another way to increase $C_{electrochemical}$ is by increasing the base surface area of working electrode 1102. For example, if the working electrode has a cylindrical shape, then the base surface area of the cylinder may be increased. In another example, if the working electrode has a rectangular prism shape, then the base surface area of the rectangular prism may be increased. However, cell 1100 has a number of drawbacks. Working electrode 1102 and lipid bilayer 1114 have the same (or similar) base surface area or cross sectional area. When the base surface area of working electrode 1102 is increased, the base surface areas of the opening of well 1105 and lipid bilayer 1114 are both increased as well. As a result, both $C_{membrane}$ and $C_{electrochemical}$ are increased simultaneously. In other words, to optimize the overall system performance, $C_{membrane}$ cannot be reduced while maximizing $C_{electrochemical}$ by adjusting the base area of well 1105 alone. In addition, the current that can be supported by working electrode 1102 is limited when the dimensions of cell 1100 are shrunk to allow greater device density. Typical electrodes can support 1-10 $mA/cm^2$ of current density. Given this current density limitation, a nanopore array with a 1 μm pitch or 100 nm pitch can supply a maximum of 100 pA current per cell or 1 pA current per cell, respectively. Resolving signals at such low current levels is challenging because the signals can be severely distorted by noise.

In the present application, an electrochemical cell for nucleic acid sequencing that has a bowl-shaped (can also be lidless box-shaped, cup-shaped or bucket-shaped) working electrode that can support an increased current in the cell is disclosed. The bowl-shaped working electrode has a planar portion at the bottom, forming the base of the bowl. The bowl-shaped working electrode further includes a surrounding wall extending perpendicular to (or at an angle from) the planar portion and along the periphery of the planar portion. Both the upper surface of the planar portion and the interior surface of the surrounding wall provide an electrode surface area that is exposed to the electrolyte 1106. As a result, the base surface area of the opening to the well (which is the same as the base surface area of the lipid bilayer) and the surface area of the working electrode that is exposed to the electrolyte can be adjusted independently of each other. Therefore, the base surface area of the opening to the well and the surface area of the bowl-shaped electrode may be adjusted independently to provide the desired ratio between $C_{membrane}$ and $C_{electrochemical}$ for optimized cell performance.

Figure 12:
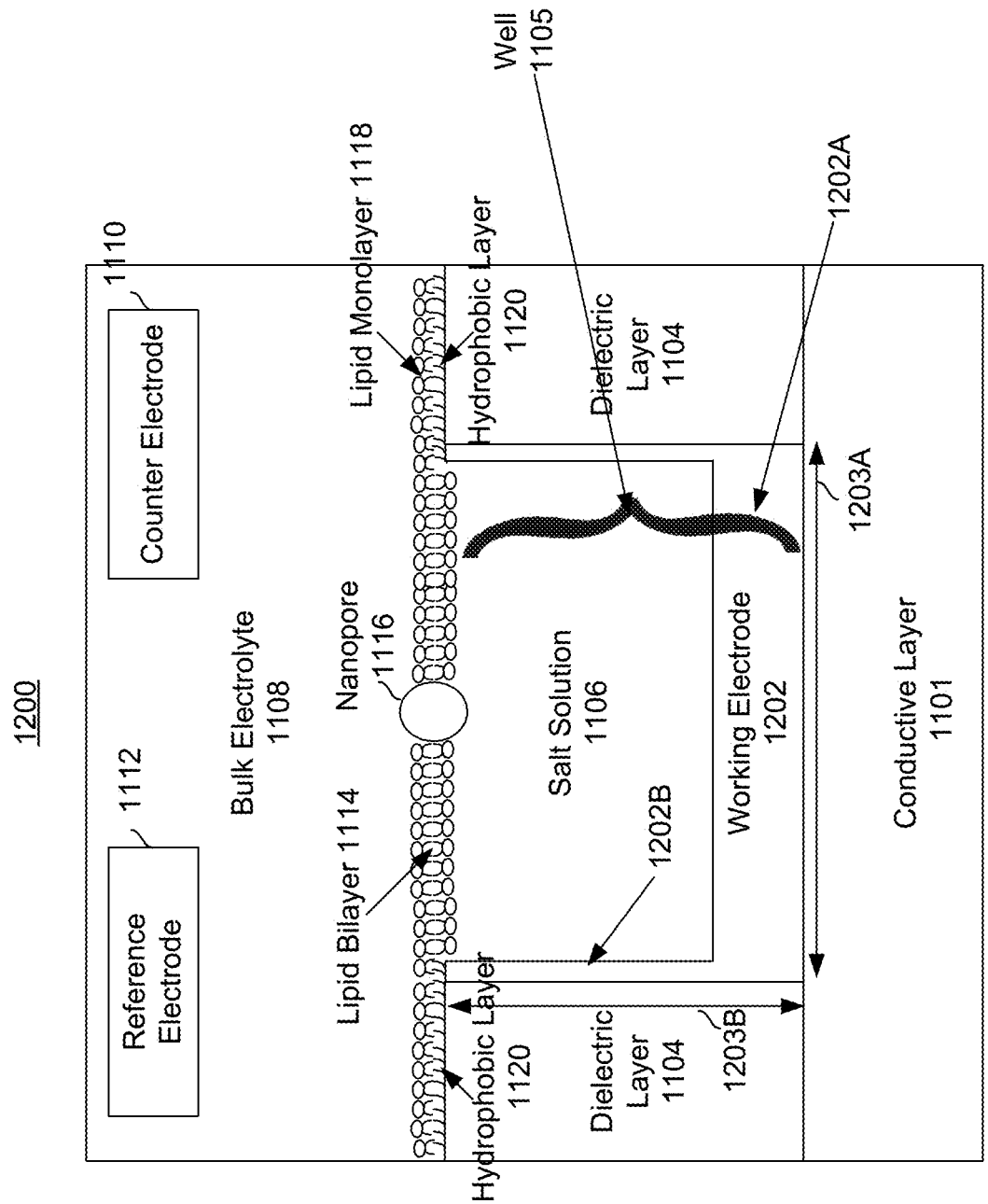
FIG. 12 illustrates an embodiment of an electrochemical cell 1200 for nucleic acid sequencing that has a bowl-shaped or lidless box-shaped working electrode that can provide an increased current in the cell.

FIG. 12 illustrates an embodiment of an electrochemical cell 1200 for nucleic acid sequencing that has a bowl-shaped or cup-shaped working electrode that can provide an increased current in the cell. Cell 1200 is one of the cells in a nanopore based sequencing chip. Cell 1200 includes a plurality of similar components as cell 1100, as indicated by identical numerals in FIGS. 11 and 12.

One difference between cell 1100 and cell 1200 is the shape and construction of their respective working electrodes (1102 and 1202). Working electrode 1102 of cell 1100 is a planar electrode located at the bottom of well 1105. Working electrode 1202 of cell 1200 is a bowl-shaped electrode; it can also be lidless box-shaped, cup-shaped or bucket-shaped. The bowl-shaped working electrode 1202 has a planar portion 1202A at the bottom, forming the base of the bowl. The base surface area may be circular or octagonal in shape. The bowl-shaped working electrode 1202 further includes a surrounding wall 1202B extending perpendicular to (or at an angle from) the planar portion and along the periphery of the planar portion. Both the upper surface of the planar portion 1202A and the interior surface of the surrounding wall 1202B provide an electrode surface area that is exposed to the electrolyte 1106. The surrounding wall 1202B takes advantage of the vertical device real estate, i.e., the space orthogonal to the substrate plane. The width (or diameter) of the planar portion 1202A is indicated by 1203A of FIG. 12, and the height of the surrounding wall 1202B is indicated by 1203B of FIG. 12. In some embodiments, width 1203A is between 1 to 100 microns, and height 1203B is between 100 nm to 20 microns. In one embodiment, width 1203A is about 5.5 microns and height 1203B is about 3.5 microns. The ratio between 1203B and 1203A is referred to as the aspect ratio of working electrode 1202. The aspect ratio may be smaller or greater than one.

Working electrode 1202 can provide an increased current in cell 1200 as compared to working electrode 1102 in cell 1100. In the case of cell 1100, assuming that the nanopore based sequencing chip has a 100 nm pitch, the working electrode 1102 has a cylindrical shape, and the current density is 10 mA/cm², cell 1100 can generate about 0.8 pA of current. In the case of cell 1200, assuming a 10:1 aspect ratio, a height 1203B of 1 micron, and a total electrode surface area of 40 times that of electrode 1102, cell 1200 can generate about 32 pA of current, thereby increasing the current by a factor of 40 or above. In some embodiments, the current that can be provided to cell 1200 may be tuned by adjusting the aspect ratio of working electrode 1202.

Working electrode 1202 can also provide an increased $C_{electrochemical}$ as compared to working electrode 1102 in cell 1100. Both the upper surface of planar portion 1202A and the interior surface of surrounding wall 1202B of electrode 1202 provide an electrode surface area that is exposed to the electrolyte 1106, thereby increasing $C_{electrochemical}$ associated with working electrode 1202. In some embodiments, the ratio of the capacitance associated with the membrane (see $C_{membrane}$ 706 of FIGS. 7A and 7B) and the capacitance associated with the working electrode (see $C_{electrochemical}$ 716 of FIGS. 7A and 7B) may be adjusted to achieve optimal overall system performance by adjusting the aspect ratio of working electrode 1202.

Figure 13:
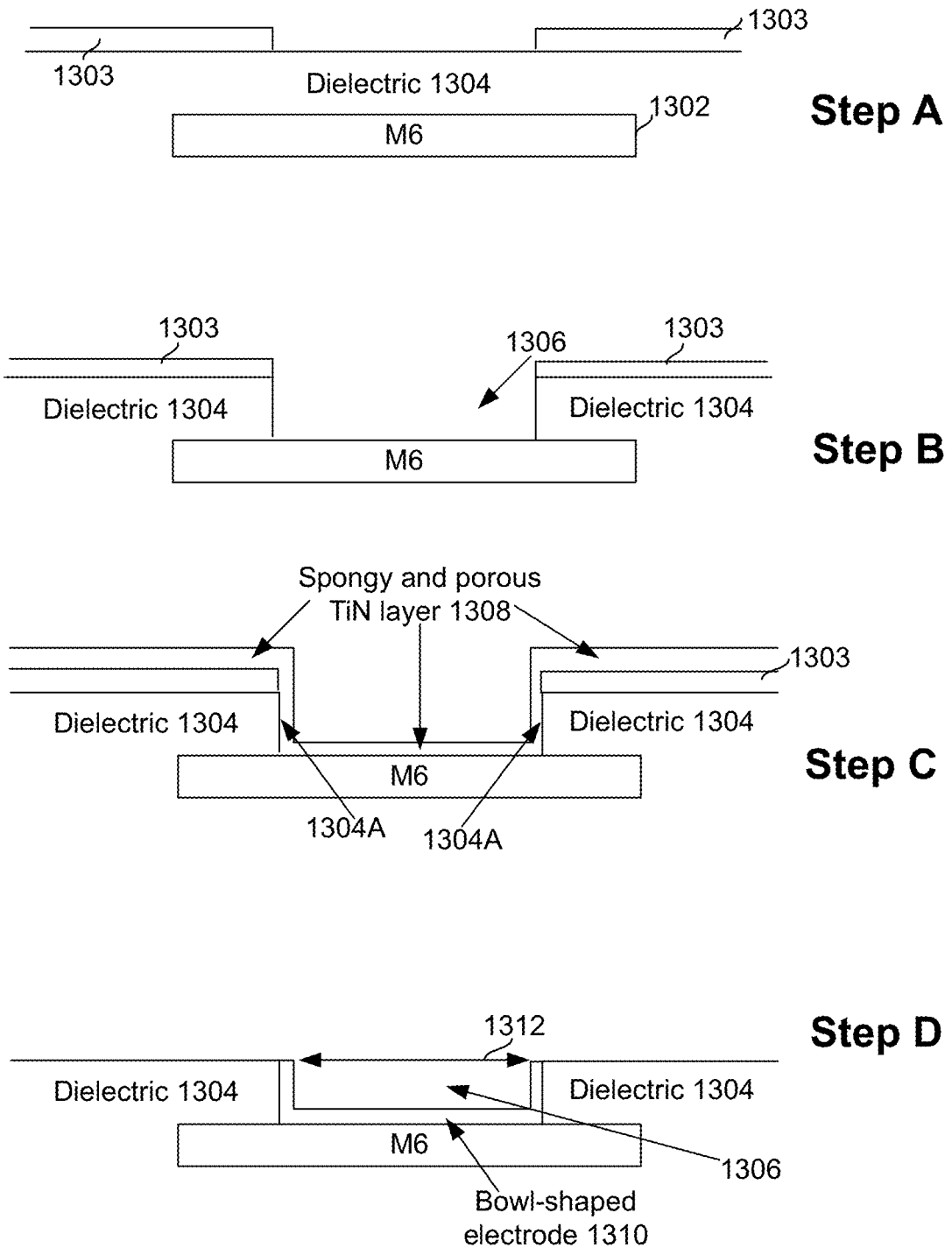
FIG. 13 illustrates an embodiment of a process for constructing an electrochemical cell of a nanopore based sequencing chip that includes a bowl-shaped or cup-shaped working electrode that can provide an increased current in the cell.

FIG. 13 illustrates an embodiment of a process for constructing an electrochemical cell of a nanopore based sequencing chip that includes a bowl-shaped or cup-shaped working electrode that can provide an increased current in the cell.

At step A, a layer of dielectric 1304 (e.g., $SiO_2$ or $Si_3N_4$) is disposed on top of a conductive layer 1302 (e.g, M6). The conductive layer includes circuitries that deliver the signals from the cell to the rest of the chip. For example, the circuitries deliver signals from the cell to an integrating capacitor. In some embodiments, the layer of dielectric 1304 has a thickness of about 400 nm. A photoresist mask 1303 is deposited above dielectric layer 1304. Photoresist mask 1303 includes a pattern for etching a well.

At step B, the layer of dielectric 1304 is etched to create a well 1306. For example, the well may be etched by chemically selective reactive-ion etching (RIE). The well 1306 provides a space for growing a spongy and porous electrode, e.g., a spongy and porous titanium nitride (TiN) electrode or platinum electrode.

At step C, a spongy and porous TiN layer 1308 is deposited to fill a portion of well 1306 created at step B. TiN layer 1308 further covers the side vertical wall 1304A of dielectric 1304. TiN layer 1308 also covers the top surface of photoresist mask 1303. In some embodiments, the spongy and porous TiN layer is grown and deposited in a manner to create rough, sparsely-spaced TiN columnar structures or columns of TiN crystals that provide a high specific surface area that can come in contact with an electrolyte. The layer of spongy and porous TiN layer can be deposited using different deposition techniques, including atomic layer deposition, chemical vapor deposition, physical vapor deposition (PVD) sputtering deposition, and the like. The TiN layer may also be deposited by PVD sputtering deposition. For example, titanium can be reactively sputtered in an $N_2$ environment or directly sputtered from a TiN target. The conditions of each of the deposition methods may be tuned in such a way to deposit sparsely-spaced TiN columnar structures or columns of TiN crystals. For example, when the TiN layer is deposited by DC (direct current) reactive magnetron sputtering from a titanium (Ti) target, the deposition system can be tuned to use a low temperature, low substrate bias voltage (the DC voltage between the silicon substrate and the Ti target), and high pressure (e.g., 25 mT) such that the TiN can be deposited more slowly and more gently to form columns of TiN crystals.

At step D, the photoresist mask 1303 is removed by a lift-off process. The lift-off process removes the portion of TiN layer 1308 that covers the top surface of photoresist mask 1303, but not the portions of TiN layer 1308 in the interior of the well. The remaining portions of TiN layer 1308 form a bowl-shaped electrode 1310. At the bottom of well 1306, there is a planar portion of the bowl-shaped electrode 1310. Coated on the surrounding wall of well 1306 (which is also the side wall of dielectric layer 1304) is the surrounding wall portion of the electrode 1310. The empty space in bowl-shaped electrode 1310 holds an electrolyte. Well 1306 has an opening 1312. A lipid bilayer can be formed to span across opening 1312. In some embodiments, the top surface of dielectric layer 1304 may be silanized. Silanization forms a hydrophobic layer above the top surface of dielectric layer 1304. The hydrophobic layer provides a surface for facilitating a membrane to form atop well 1306 and to span across the opening 1312 of the well. In some embodiments, the hydrophobic layer extends downward partially into well 1306 and covers part of the sidewall of the well to further facilitate a membrane to form atop the well and to span across the opening 1312 of the well.

Electrode 1310 provides a capacitively-coupled non-faradaic electrode, as TiN has a high capacitance and large working window in aqueous solution. However, if charge transfer is required, step C can be modified to deposit another material, such as platinum, that is more suitable for faradaic reactions to form the working electrode.

Figure 14:
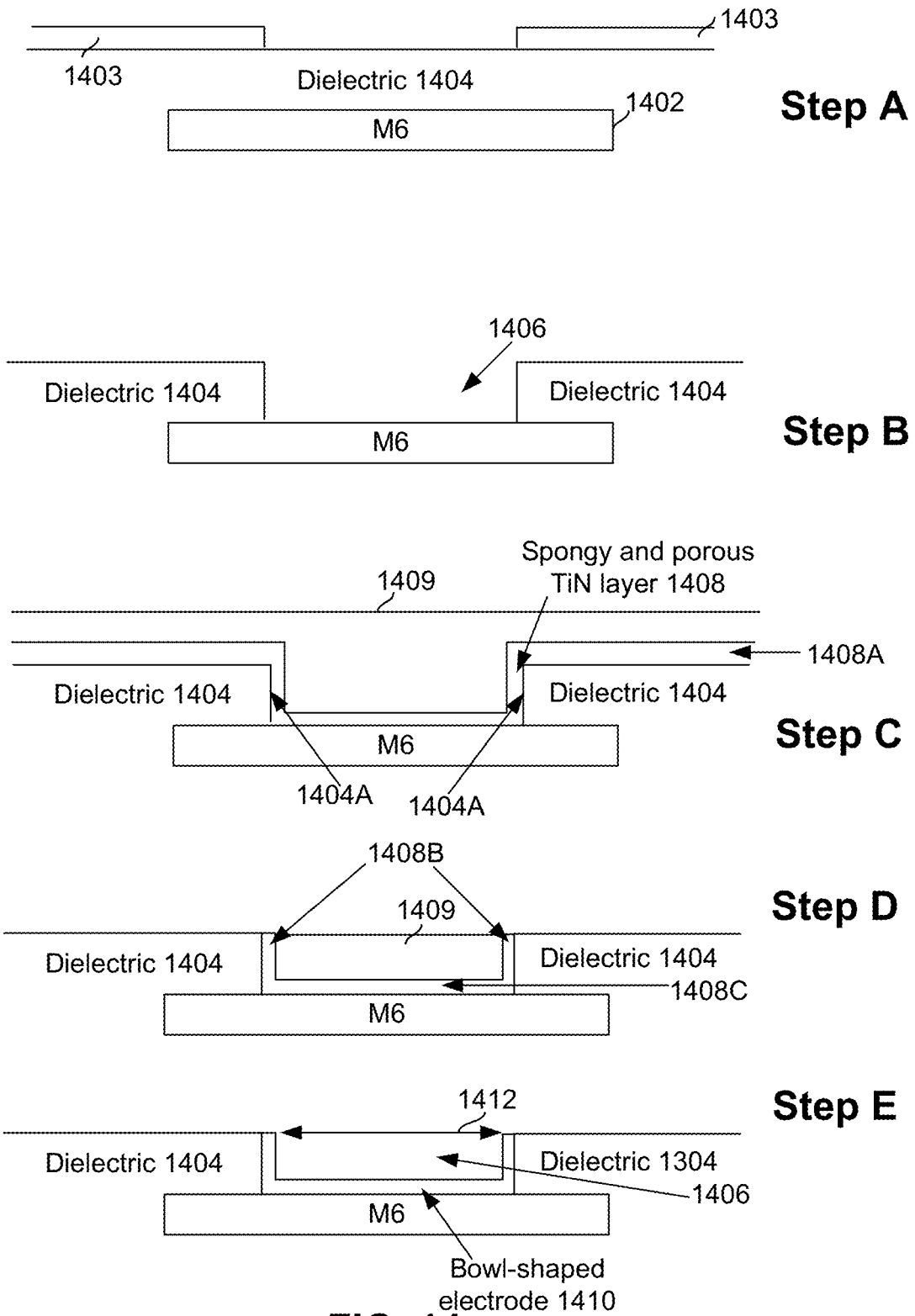
FIG. 14 illustrates another embodiment of a process for constructing an electrochemical cell of a nanopore based sequencing chip that includes a bowl-shaped or cup-shaped working electrode that can provide an increased current in the cell.

FIG. 14 illustrates another embodiment of a process for constructing an electrochemical cell of a nanopore based sequencing chip that includes a bowl-shaped or cup-shaped working electrode that can provide an increased current in the cell.

At step A, a layer of dielectric 1404 (e.g., $SiO_2$ or $Si_3N_4$) is disposed on top of a conductive layer 1402 (e.g, M6). The conductive layer includes circuitries that deliver the signals from the cell to the rest of the chip. For example, the circuitries deliver signals from the cell to an integrating capacitor. In some embodiments, the layer of dielectric 1404 has a thickness of about 400 nm. A photoresist mask 1403 is deposited above dielectric layer 1404. Photoresist mask 1403 includes a pattern for etching a well.

At step B, the layer of dielectric 1404 is etched to create a well 1406. For example, the well may be etched by chemically selective reactive-ion etching (RIE). The well 1406 provides a space for growing a spongy and porous electrode, e.g., a spongy and porous TiN electrode or platinum electrode. Photoresist mask 1403 is removed.

At step C, a spongy and porous TiN layer 1408 is deposited to fill a portion of well 1406 created at step B. TiN layer 1408 further covers the vertical wall 1404A of dielectric 1404 and well 1406. TiN layer 1408 also covers the top surface of dielectric layer 1404. In some embodiments, the spongy and porous TiN layer is grown and deposited in a manner to create rough, sparsely-spaced TiN columnar structures or columns of TiN crystals that provide a high specific surface area that can come in contact with an electrolyte. The layer of spongy and porous TiN layer can be deposited using different deposition techniques, including atomic layer deposition, chemical vapor deposition, physical vapor deposition (PVD) sputtering deposition, and the like. The TiN layer may also be deposited by PVD sputtering deposition. For example, titanium can be reactively sputtered in an $N_2$ environment or directly sputtered from a TiN target. The conditions of each of the deposition methods may be tuned in such a way to deposit sparsely-spaced TiN columnar structures or columns of TiN crystals. For example, when the TiN layer is deposited by DC (direct current) reactive magnetron sputtering from a titanium (Ti) target, the deposition system can be tuned to use a low temperature, low substrate bias voltage (the DC voltage between the silicon substrate and the Ti target), and high pressure (e.g., 25 mT) such that the TiN can be deposited more slowly and more gently to form columns of TiN crystals. A layer of sacrifical layer 1409 is deposited. In some embodiments, sacrificial layer 1409 is a layer of tungsten or nickel. Sacrificial layer 1409 fills well 1406 and covers the portion of TiN layer 1408 (1408A) that covers the top surface of dielectric layer 1404.

At step D, the excess sacrifical layer 1409 and the excess TiN layer 1408A are removed, for example by chemical mechanical polishing (CMP) techniques, to create a coplanar surface. The remaining bottom TiN portion 1408C and the remaining vertical wall TiN portion 1408B form a spongy and porous TiN working electrode 1410. The diameter or width of working electrode 1410 is between 20 nm to 100 microns.

At step E, sacrificial layer 1409 is isotropically etched to open up well 1406 with an opening 1412. The remaining portions of TiN layer 1408 (1408B and 1408C) form a bowl-shaped electrode 1410. Sacrificial layer 1409 is made of a material that is differentially etchable from dielectric layer 1404 and electrode 1410. In some embodiments, sacrificial layer 1409 is made of tungsten, and a selective etchant such as hot $H_2O_2$ is used as the wet etchant. The wet etchant selectively etches sacrificial layer 1409 without damaging dielectric layer 1404 and electrode 1410. The advantage of using a sacrificial layer 1409 is that the etching process is more robust and the process requires less tuning because over etching does not damage dielectric layer 1404 or working electrode 1410.

At the bottom of well 1406, there is a planar portion of the bowl-shaped electrode 1410. Coated on the surrounding wall of well 1406 (also the side wall of dielectric layer 1304) is the surrounding wall portion of the electrode 1410. The empty space in bowl-shaped electrode 1410 holds an electrolyte. Well 1406 has an opening 1412. A lipid bilayer can be formed to span across opening 1412.

Figure 15:
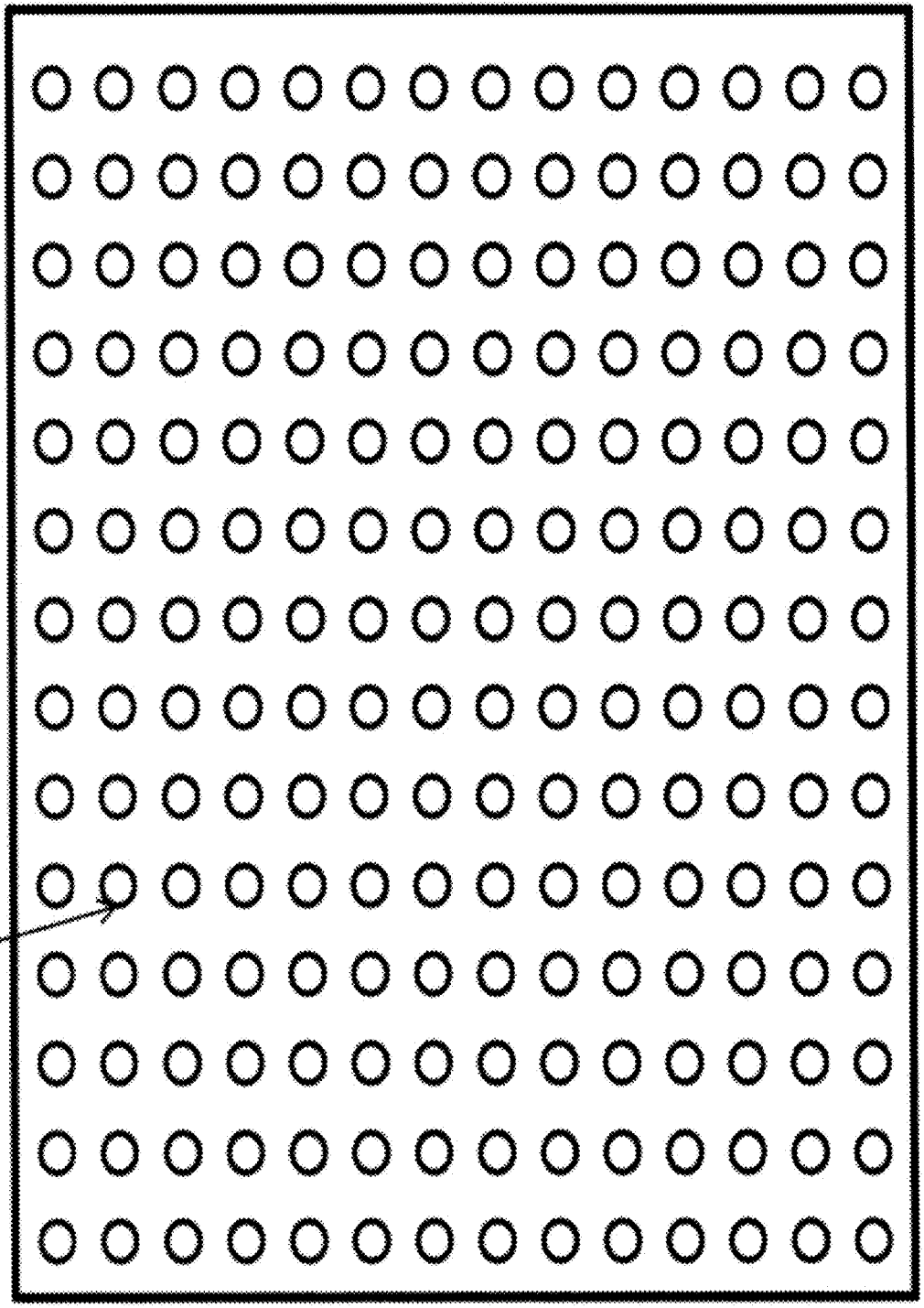
FIG. 15 illustrates a top view of a plurality of circular openings 1502 of a plurality of wells in a nanopore based sequencing chip.

FIG. 15 illustrates a top view of a plurality of circular openings 1502 of a plurality of wells in a nanopore based sequencing chip. In some embodiments, opening 1502 above the working electrode is octagonal in shape.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A nanopore cell, including:
   an electrolyte well having a bottom base, a surrounding dielectric sidewall having a first surface that faces an interior volume of the electrolyte well and a second surface that is planar and parallel to the bottom base of the electrolyte well;
   a first portion of electrode material disposed on the bottom base of the electrolyte well, wherein the first portion of electrode material covers the entire bottom base of the electrolyte well; and
   a second portion of electrode material disposed on the first surface of the surrounding dielectric sidewall of the electrolyte well and electrically connected to the first portion of electrode material, the second portion of electrode material having a first surface that faces the interior volume of the electrolyte well and a second surface that forms an annulus that is coplanar with the second surface of the surrounding dielectric sidewall; and wherein the first portion of electrode material and the second portion of electrode material are configured to jointly provide capacitive coupling when an electrolyte is placed in the electrolyte well; and wherein the first portion of electrode material forms a base portion of a working electrode, and wherein the second portion of electrode material forms a surrounding wall of the working electrode.

2. The nanopore cell of claim 1, and wherein a width of the base portion of the working electrode is between 1 to 100 microns.

3. The nanopore cell of claim 1, and wherein a height of the surrounding wall of the working electrode is between 100 nm to 20 microns.

4. The nanopore cell of claim 1, wherein the working electrode comprises a spongy and porous TiN working electrode that is deposited by a deposition technique with conditions tuned to deposit TiN columnar structures or columns of TiN crystals.

5. The nanopore cell of claim 1, further comprising a hydrophobic surface above the surrounding dielectric sidewall, wherein the hydrophobic surface above the surrounding dielectric sidewall provides a surface for facilitating a membrane to form atop the electrolyte well, and wherein the membrane spans across an opening of the electrolyte well.

6. The nanopore cell of claim 1, wherein an aspect ratio of the working electrode comprises a ratio between a height of the surrounding wall of the working electrode and a width of the base portion of the working electrode, and wherein the aspect ratio has a range of 0.001 to 20.

* * * * *